United States Patent
Murray (10) Patent No.: US 8,348,957 B2
(45) Date of Patent: Jan. 8, 2013

(54) PIN CENTERING GUIDE WITH GONIOMETER

(75) Inventor: David W. Murray, Oxford (GB)

(73) Assignee: Wright Medical Technology, Inc., Arlington, TN (US)

(*) Notice: Subject to any disclaimer, the term of this patent is extended or adjusted under 35 U.S.C. 154(b) by 949 days.

(21) Appl. No.: 12/329,131

(22) Filed: Dec. 5, 2008

(65) Prior Publication Data

US 2009/0240253 A1 Sep. 24, 2009

Related U.S. Application Data

(60) Provisional application No. 61/012,090, filed on Dec. 7, 2007.

(51) Int. Cl.
*A61B 17/58* (2006.01)

(52) U.S. Cl. .......................... 606/96; 606/102

(58) Field of Classification Search .................. 606/104, 606/95, 258, 86 R–89, 96–98, 102; 403/52, 403/53, 55, 57, 59, 60, 68, 73, 78, 230; 16/221; 602/16; 623/22.11–22.2, 23.11–23.14
See application file for complete search history.

(56) References Cited

U.S. PATENT DOCUMENTS 5,397,323 A * 3/1995 Taylor et al. ............... 606/130
5,688,284 A * 11/1997 Chervitz et al. ............. 606/96
6,390,424 B1 * 5/2002 Kidushim et al. ........ 248/122.1
2005/0245934 A1 * 11/2005 Tuke et al. ................... 606/79
2008/0109085 A1 * 5/2008 Tulkis et al. ............. 623/22.11

FOREIGN PATENT DOCUMENTS

FR 2863859 A1 12/2003
WO WO2007/137327 A1 12/2007

OTHER PUBLICATIONS

European Search Report for EP 08021155 dated Dec. 5, 2008.

* cited by examiner

*Primary Examiner* — Kevin T Troung
*Assistant Examiner* — Diana S Jones
(74) *Attorney, Agent, or Firm* — Duane Morris LLP (57) ABSTRACT

An instrument assembly for placing a guide pin in a femoral neck of a patient with reference to a medullary guide wire for use in resurfacing a femoral head. The assembly comprises a femoral neck clamp configured to define a femoral neck center. A pin guide attaches to the femoral neck clamp. A pin guide portion of the pin guide is configured to define a pin guide path passing through the neck center. The pin guide portion is linked to pin guide engagement portion of an adjustable goniometer. The goniometer maintains a specific angle between the pin guide engagement portion and the medullary guide wire, and in turn maintains the pin guide path at the specific angle.

18 Claims, 7 Drawing Sheets

PIN CENTERING GUIDE WITH GONIOMETER

CROSS REFERENCE TO RELATED APPLICATIONS

This application is a continuation of, claims priority to, and incorporates by reference U.S. Provisional Patent Application No. 61/012,090, filed Dec. 7, 2007.

STATEMENT REGARDING FEDERALLY SPONSORED RESEARCH

Not applicable

FIELD OF THE INVENTION

The present invention relates to the use of guides for placement of guide wires or pins in orthopedic surgery, and more particularly to the use of instruments for the placement of a guide pin in a femoral neck for use in femoral head resurfacing.

BACKGROUND OF THE INVENTION

In total hip arthroplasty, the head and neck of the femur are removed and replaced with a femoral stem prosthesis, along with a matching cup in the acetabulum. Barring complications, a total hip replacement provides a patient with a hip joint that functions much like the natural hip joint, typically for a 20 to 30 year period. However, over time, the implant may wear out or loosen. In such cases, it becomes necessary to replace the original hip joint prosthesis through a revision surgery. Successful revision of a primary total hip prosthesis can be challenging because there is less natural bone to work with, due to the previous removal of the head and neck and neck, and the loss of bone in the area of the primary implant.

For younger patients, it is often desirable to delay total hip arthroplasty in order to preserve bone mass and minimize the risk of requiring a first and possibly a second revision procedure later in life. This can be accomplished by using a resurfacing femoral implant, such as the type disclosed in U.S. Pat. No. 4,123,806 (Amstutz et al.). A resurfacing implant preserves the femoral neck and most of the femoral head. Femoral head resurfacing procedures typically rely upon the placement of a guide pin in the femoral neck. The guide pin protrudes from the femoral head, where it serves as a drive axis for accurate reaming of the surface of the femoral head for receipt of the resurfacing femoral implant. Once the femoral head has been shaped to receive the resurfacing femoral implant, the guide pin is removed. Pin placement theory is based on four primary criteria: (1) in the coronal plane, the pin is centered in the neck in order to prevent notching; (2) in the coronal plane, the pin is either placed centrally in the neck or at a templated angle, such as 140 degrees; (3) in the transverse plane, the pin is centered in the neck; and (4) in the transverse plane, the pin is placed so as to retain neck anteversion, unless the neck is very anteverted.

A guide pin can be placed in the femoral neck without the use of guide instruments. Using external imaging in the coronal and transverse planes, the surgeon identifies the center of the femoral neck, ignoring the location of the femoral head. Diathermy can be used to mark up the center of the femoral neck at about 140 degrees in the coronal plane. The guide wire is then passed into the femoral head.

Placement of the guide pin by eye can provide good results, particularly when performed by a surgeon skilled in hip resurfacing. However, placement by eye can also lead to inaccuracy or inconsistency in pin placement, and therefore to less than optimal results, particularly when practiced by an inexperienced surgeon. Therefore, efforts have been made to provide instruments for use in accurately positioning the guide pin in the femoral neck. Examples include U.S. Pat. No. 6,156,069 (Amstutz et al.) and WO 2005/051,209 A1 (Sheldon et al.), both of which are commonly assigned and are incorporated herein by reference.

Despite the advantages provided by the instruments disclosed in U.S. Pat. No. 6,156,069 (Amstutz et al.) and WO 2005/051,209, further improvements in the adjustability of positioning of pins and guide wires to improve the accurate placement of femoral prostheses are desirable. Applicants have made previous use of the femoral neck clamps and pin guides of the type shown in FIGS. 7-8. The femoral neck clamp reliably guides the guide pin through the center of the femoral neck and minimizes the risk of notching during reaming of the femoral head. However, the femoral neck clamp does not guide varus/valgus or anteversion. Varus/valgus or anteversion can be obtained by eye by alignment with the neck or through the use of a protractor. Applicants have also experimented with the use of a nonadjustable goniometer to achieve accurate varus/valgus and anteversion. In doing so, applicants discovered the desireability of providing an adjustable goniometer and instrument assembly having the features and advantages described herein.

OBJECTS AND SUMMARY OF THE INVENTION

It is an object of the invention to provide an instrument assembly including a clamp and goniometer for use in pin guide placement.

It is another object of the invention to provide femoral pin guide placement instruments that determine component position, and avoid fractures, loosening and impingement.

It is another object of the invention to provide femoral guide pin placement instruments that enable accurate pin placement to be achieved the first time, with no need to check or adjust.

It is another object of the invention to provide femoral guide pin placement instruments and related techniques of use that are simple, reliable and cope with all cases e.g. large osteophytes, abnormal varus/valgus or anteversion.

It is yet another object of the invention to provide femoral guide pin placement instruments that work with all approaches, including MIS approaches.

The foregoing and other objects and advantages are achieved by providing an instrument assembly for placing a guide pin in a femoral neck of a patient with reference to a medullary guide wire for use in resurfacing a femoral head. The assembly comprises, generally, a femoral neck clamp, a pin guide, and a goniometer linked to the pin guide. The femoral neck clamp is configured to define a neck center of the femoral neck. The pin guide is attached to the femoral neck clamp. The pin guide has a pin guide portion. The pin guide portion is configured to define a pin guide path passing through the neck center defined by the femoral neck clamp. The goniometer has a medullary guide wire engagement member and a pin guide engagement portion. The pin guide engagement portion is adjustably linked to the medullary guide wire engagement member so as to accommodate patients of various sizes. The pin guide engagement portion is configured to maintain a set angle with respect to the medullary guide wire. The pin guide engagement portion and the pin guide portion are configured to engage one another such that the goniometer orients the pin path at the set angle with respect to the medullary guide wire. The goniometer may have an angle adjustment member, the angle adjustment member configured to adjust the pin guide engagement portion between a plurality of set angles, such as 135 degrees, 140 degrees, and 145 degrees. The goniometer can be linked to the pin guide by a pin guide bushing, the pin guide bushing having a through bore configured to closely receive the guide pin. Various other features of the instruments, along with methods of using the instrument, are described below.

The foregoing and other objects, features, aspects and advantages of the invention will become more apparent from the following detailed description of the invention when considered in conjunction with the accompanying drawings.

DETAILED DESCRIPTION OF THE INVENTION

In the following detailed description of the preferred embodiments, reference is made to the accompanying drawings which form a part hereof, and in which are shown by way of illustration specific embodiments in which the invention may be practiced. It is to be understood that other embodiments may be utilized and structural changes may be made without departing from the scope of the present invention.

Figure 1:
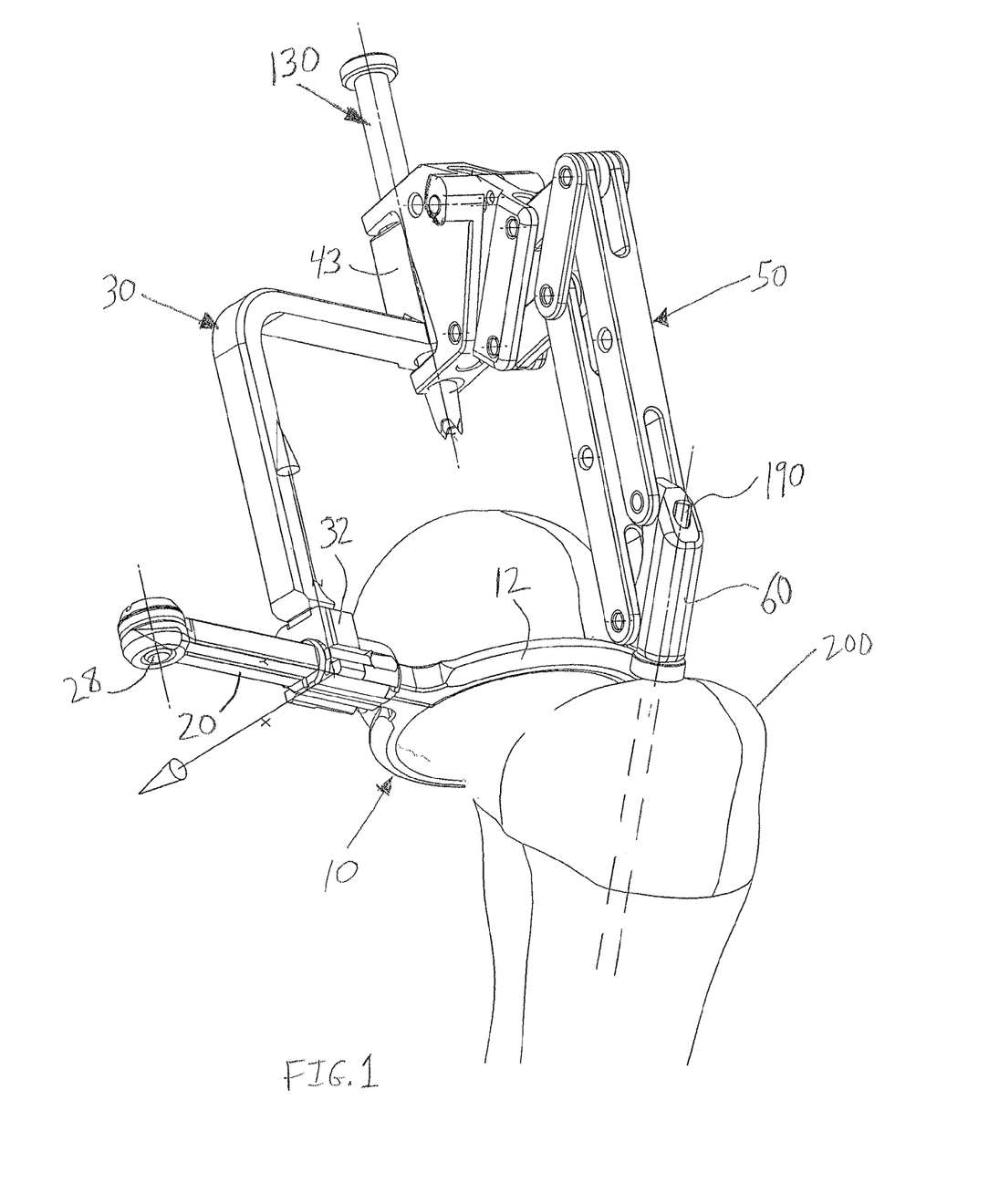
FIG. 1 is a perspective view of one embodiment of an instrument assembly of the invention.

As shown in FIG. 1, the invention is an assembly for placing a guide pin 180 in a femoral neck 202 of a patient for subsequent use in resurfacing a femoral head 204. The assembly is configured so as to enable the orientation of the guide pin 180 to be established with reference to a medullary guide wire 190. The assembly includes, generally, a femoral neck clamp 10, a pin guide 30, and a goniometer 50. A bushing 130 links the pin guide 30 to the goniometer 50. As indicated in the representational view of FIG. 2, the femoral neck clamp 10 is configured to define a pin point C coinciding with a center of the femoral neck 202. As shown in FIG. 1, the pin guide 30 attaches to the femoral neck clamp 10. The pin guide 30 has a pin guide portion 43 which is configured to define a pin guide path P passing through the pin point C defined by the femoral neck clamp 10. The goniometer 50 has a medullary guide wire engagement member 60 and a pin guide engagement portion 102. The pin guide engagement portion 102 is configured to maintain a set angle with respect to the medullary guide wire 190. As indicated in the representational view of FIG. 2, the pin guide engagement portion 102 and the pin guide portion 43 are configured to engage one another such that the goniometer orients the pin guide path P at the set angle with respect to the medullary guide wire 190. As indicated in the representational view of FIG. 2, the pin guide engagement portion 102 is adjustably linked to the medullary guide wire engagement member 60 so as to accommodate patients of various sizes. While various adjustable linkage means could be used for this purpose, as indicated by the representational views, a four bar linkage embodiment will be discussed in detail below.

In the embodiment shown in FIG. 1, the pin guide engagement portion 102 of the goniometer 50 and the pin guide portion 43 of the pin guide 30 are configured to receive a pin guide bushing 130 therethrough. The pin guide bushing 130 links the goniometer 50 and the pin guide 30 along the pin path P. The pin guide 30 is rotatably attached to the femoral neck clamp 10, such that the pin guide portion 43 can be selectively rotated through a plurality of guide pin angles or paths P, with each of the guide pin angles passing through the neck center C defined by the femoral neck clamp 10.

Figure 4:
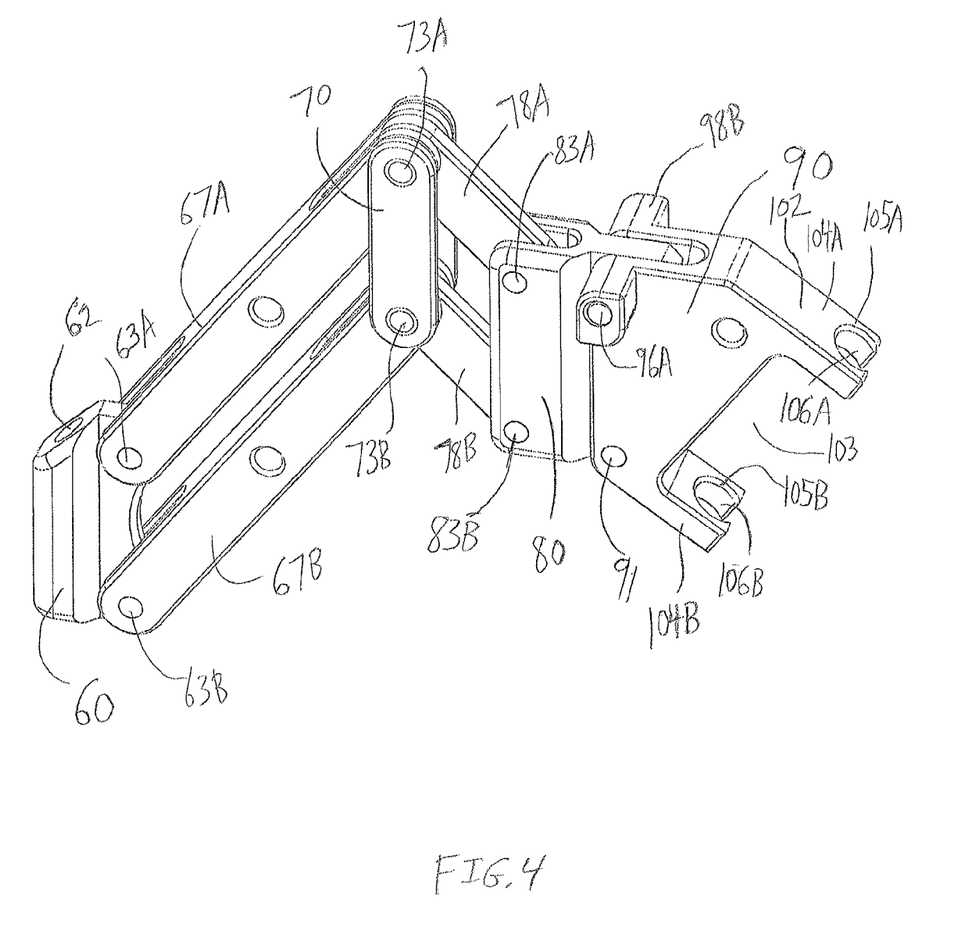
FIG. 4 is a perspective view of one embodiment of a goniometer of the invention.
Figure 5A:
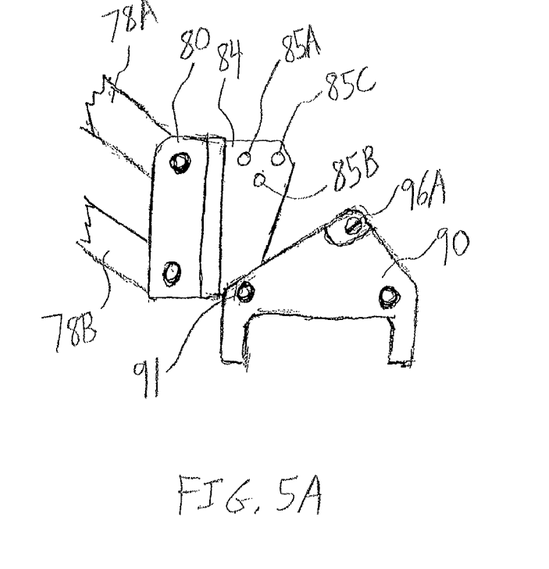
FIG. 5A is a side view of one embodiment of an adjustment component of a goniometer of the invention in an open, unengaged position.
Figure 5B:
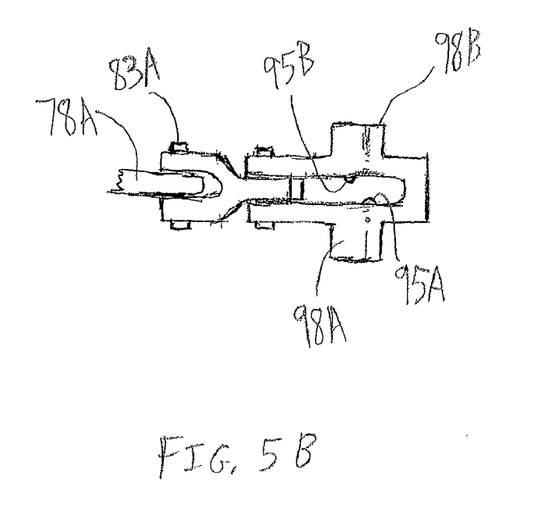
FIG. 5B is a side view of one embodiment of an adjustment component of a goniometer of the invention in an engaged position.
Figure 6A:
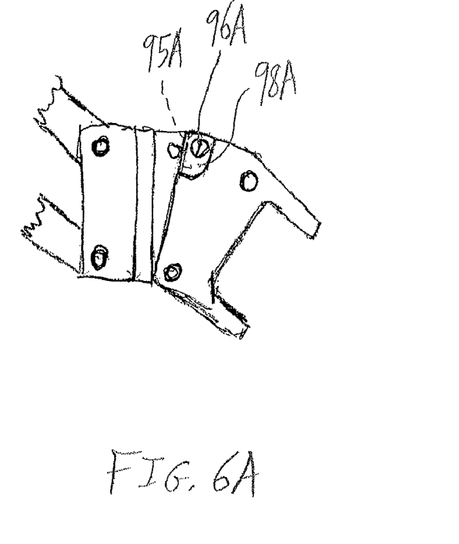
FIG. 6A is a top view of one embodiment of an adjustment component of a goniometer of the invention in an open, unengaged position.
Figure 6B:
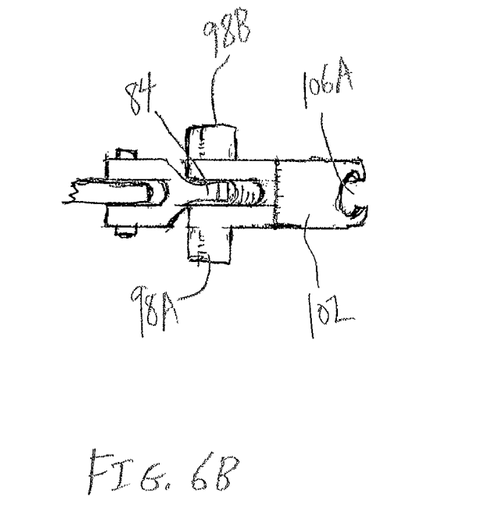
FIG. 6B is a top view of one embodiment of an adjustment component of a goniometer of the invention in an engaged position.

As shown in FIG. 4, the goniometer 50 can have an angle adjustment member 90. As shown in FIGS. 5A-6B, the angle adjustment member 90 is configured to adjust the pin guide engagement portion 102 between a plurality of set angles. In the embodiment of FIGS. 5-6, the angle adjustment member 90 is configured to adjust the pin guide engagement portion 102 between three set angles, the angles being 135 degrees, 140 degrees and 145 degrees with respect to the medullary guide wire 190. The angle adjustment member 90 feature reduces instrument inventory, since it is not necessary to provide separate goniometers having different angles.

Figure 7A:
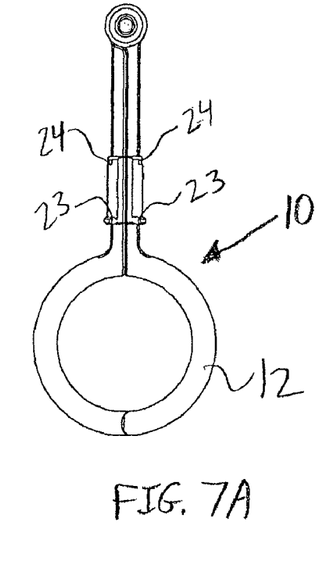
FIG. 7A is a side view of one embodiment of femoral neck clamp for use in the instrument assembly of the invention.
Figure 7B:
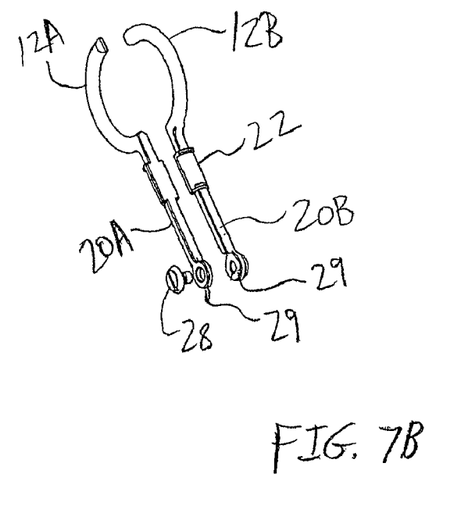
FIG. 7B is an exploded view of one embodiment of femoral neck clamp for use in the instrument assembly of the invention.

The femoral neck clamp 10 has a ring portion 12 and an extension portion 20 extending from the ring portion 12. As shown in FIG. 7, the ring portion 10 includes a first partial ring portion 12A and a second partial ring portion 12B. The first partial ring portion 12A has a first extension portion 20A extending therefrom, while the second partial ring portion 12B has a second extension portion 20B extending therefrom. As shown in FIG. 7B, the first and second extension portions 20A, 20B are pivotally attached to one another, such as by end bores 29 jointed by a pivot bolt 28.

The extension portion 20 of the femoral neck clamp 10 includes a track 22 for rotatable engagement with an attachment base 32 of the pin guide 30. The track 22 includes a pair of opposing stops 23 for abutting against a stop member 36 of the pin guide 30 attachment base 32 to thereby establish a rotation range for the pin guide 30 relative to the femoral neck clamp 10. The track 22 includes a tine groove 24 for engaging a tine 34 or tines of the attachment base 32 of the pin guide 30 to thereby selectively secure the pin guide 30 in the track 22 of the femoral neck clamp 10

Figures 8A, 8B:
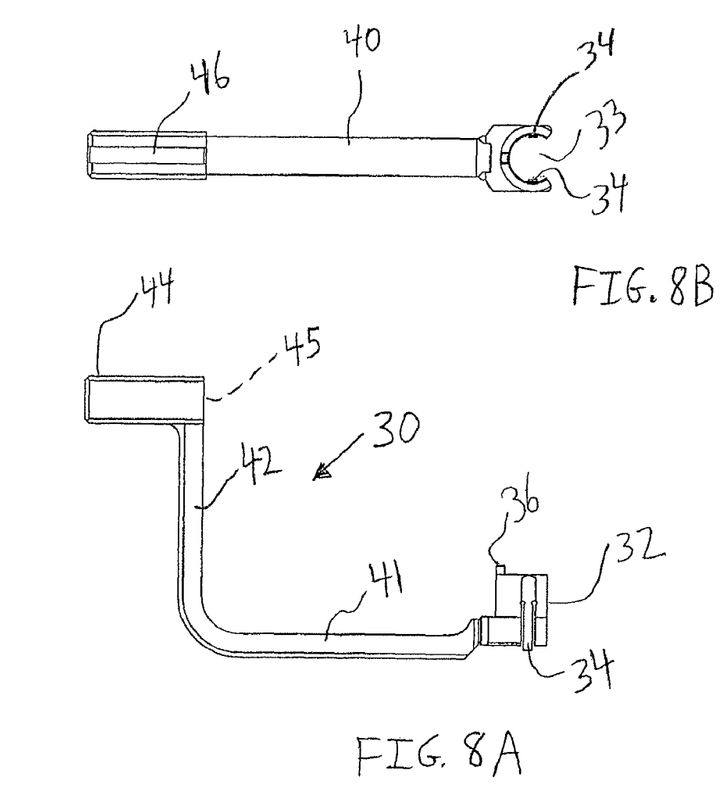
FIG. 8A is a side view of one embodiment of a pin guide for use in the instrument assembly of the invention.
FIG. 8B is a front view of one embodiment of a pin guide for use in the assembly of the invention.

As shown in FIG. 8A, the pin guide 30 has an attachment base 32. As shown in FIG. 8B, the attachment base 32 has a bore 33 therethrough for receiving the femoral neck clamp 10 in a rotatable relationship. At least one tine 34 is provided in the attachment base 32 for selectively engaging a corresponding tine groove 24 in the extension portion 20 of the femoral neck clamp 10. As shown in FIG. 8A, a stop member 36 extends from the attachment base 32.

The pin guide 30 includes an extension portion 40, which serves to properly space the pin guide portion 43 from the attachment base 32. In the embodiment of FIG. 8A, the extension portion has a first leg 41 extending from the attachment base 32 and a second leg 42 extending at an angle, such as a right angle, from the first leg 41, and thus forms an L shape.

As shown in FIG. 8A, the pin guide portion 43 is positioned at an end of the second leg 42. The pin guide portion 43 has a bushing holder 44 having a bushing bore 45 therethrough. The bushing bore 45 is sized to closely receive the pin guide bushing 130 therethrough. In the embodiment of FIG. 8B, a lengthwise slot 46 extends along and communicates with the bushing bore 45.

As shown in FIG. 1, the goniometer 50 includes a medullary guide wire engagement member 60 for use in operatively mounting the goniometer 50 on a medullary guide wire 190. The medullary guide wire engagement member 60 has a medullary guide wire bore 62 passing therethrough. The medullary guide wire bore 62 is configured to closely receive the medullary guide wire 190, such that during use, the medullary guide wire bore 62 is substantially coaxial with medullary guide wire 190.

In the embodiment shown in FIGS. 1 and 4, the pin guide engagement portion 102 is adjustably linked to the medullary guide wire engagement member 60 via a four bar linkage arrangement. The four bar linkage includes the medullary wire engagement member 60, a support member 80, and a central member 70 between the medullary wire engagement member 60 and the support member 80. The central member 70 is pivotally linked to the medullary wire engagement member 60 via a first upper linkage bar 67A and a first lower linkage bar 67B. The first bars 67A, 67B are joined to the medullary wire engagement member 60 by pivot bolts 63A, 63B, and are joined to the central member 70 by a set of central pivot bolts 73A, 73B. The central member 70 is further pivotally linked to the support member 80 via a second upper linkage bar 78A and a second lower linkage bar 78B. The second linkage bars 78A, 78B are pivotally linked to the central member 70 via the central pivot bolts 73A, 73B, and to the support member 80 via another set of pivot bolts 83A, 83B.

In the embodiment shown in FIGS. 4-5, the support member 80 has an adjustment portion 84 and an angle adjustment member 90. The angle adjustment member 90 is configured for selecting between a plurality of angles relative to the medullary guide wire 190. In the embodiment shown in FIG. 5, the angle adjustment member 90 is pivotally 91 engaged to the adjustment portion 84. The adjustment portion 84 has a first angle indent 85A, a second angle indent 85B and a third angle indent 85C. The indents 85A, 85B, 85C can be through holes.

As shown in FIG. 5B, the angle adjustment member 90 has at least one detent 95, which is configured to selectively engage the first, second and third angle indents 85A, 85B, 85C for use in selecting an angle for the angle adjustment member 90. In the embodiment of FIG. 5B, the angle adjustment member 90 has an upper detent 95A and a lower detent 95B. For ease of use, the detents 95A, 95B are preferably spring biased plunger detents. As indicated in FIGS. 5A and 6A, the spring biased plunger detents 95A, 95B are held in their respective housings by a set screw 96B.

In the embodiment of FIGS. 5B and 6B, the angle adjustment member 90 has an upper detent housing 97A and a lower detent housing 97B. In FIG. 5B, the angle adjustment member 90 is shown in an open or unengaged position, while in FIG. 6B, the angle adjustment member 90 is engaged to the indents 85A, 85B, 85C. The upper and the lower detent housings 97A, 97B are fixedly positioned on opposing sides of the angle adjustment member 90. As shown in FIG. 5A, the first and third indents 85A, 85C are positioned above the second or lower indent 85B. The upper detent 95A is positioned in the upper detent housing 97A so as to selectively engage the upper first and third indents 85A, 85C when the angle adjustment member 90 is pivoted toward the support member 80. Likewise, the lower detent 95B is positioned in the lower detent housing 97B so as to selectively engage the second or lower indent 85B. The open configuration shown in FIG. 5B further shows the staggered position of the upper and lower detents 95A, 95B with respect to one another.

In the embodiment shown in FIG. 4, the engagement portion 102 of the goniometer has an upper arm 104A and a lower arm 104B, with the arms 104A, 104B defining an opening 103 therebetween. As indicated in FIG. 1, the opening 103 is sized to receive the bushing holder 44 of the pin guide 30. The upper arm 104A has an upper bushing holder 105A adjacent an end thereof. The upper bushing holder 105A has an upper bushing bore 106A formed therethrough. The lower arm 104B likewise has a lower bushing holder 105B adjacent an end thereof, with a lower bushing bore 106B formed therethrough. The upper and lower bushing bores 106A, 106B are axially aligned for receipt of the bushing 130.

Figure 2:
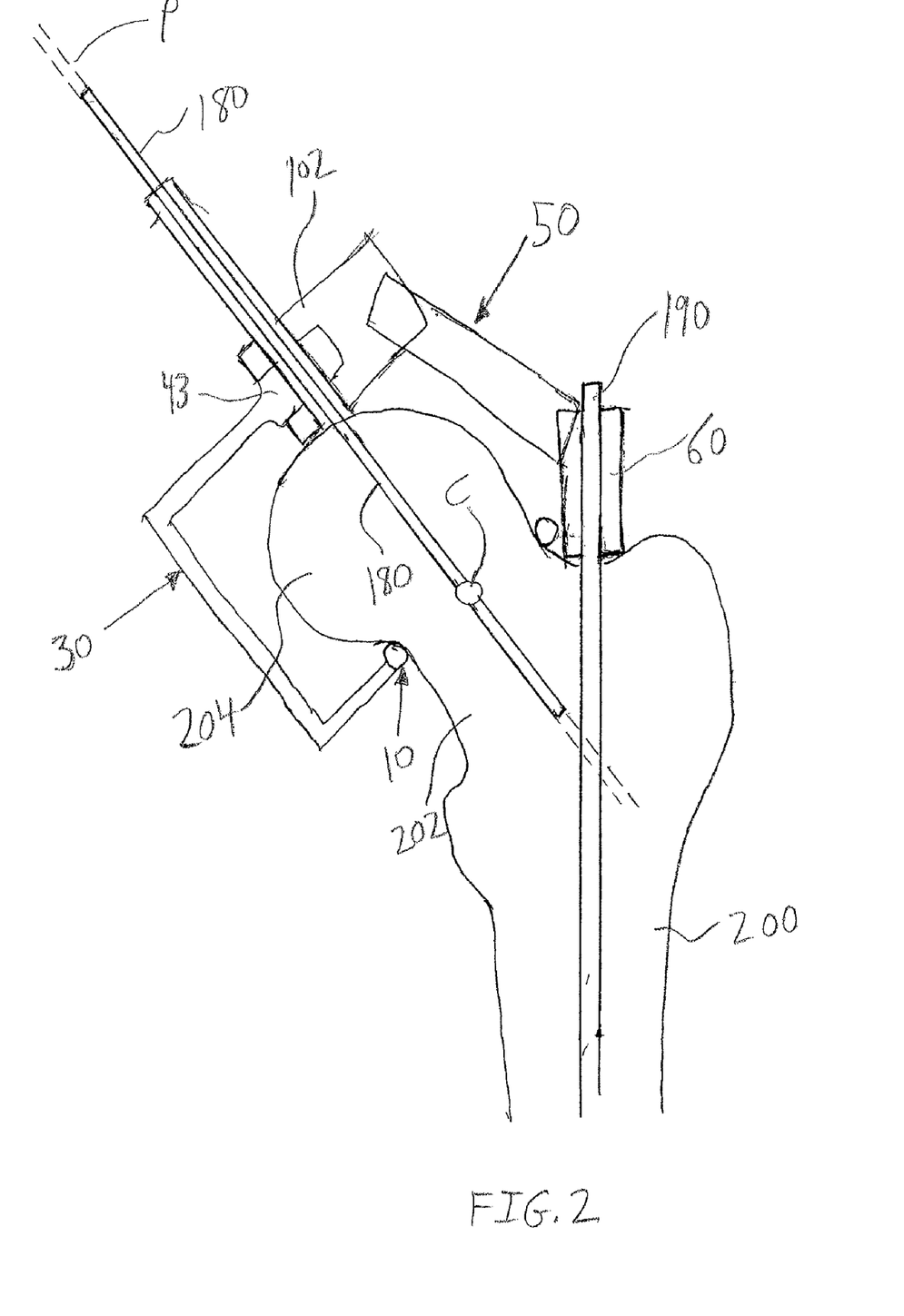
FIG. 2 is a representational view of one embodiment of an instrument assembly of the invention, shown in a coronal plane.

As indicated in FIGS. 1 and 2, the bushing 130 threads through the upper bushing bore 106A of the goniometer 50, the bushing bore 45 of the pin guide 30, and the lower bushing bore 106B of the goniometer 50. The bushing 130 links the pin guide 30 and the goniometer 50 to one another such that the bushing 130 is axially aligned along an axis that coincides with the guide pin path P and which passes through the neck center C defined by the femoral neck clamp 10.

Figure 9:
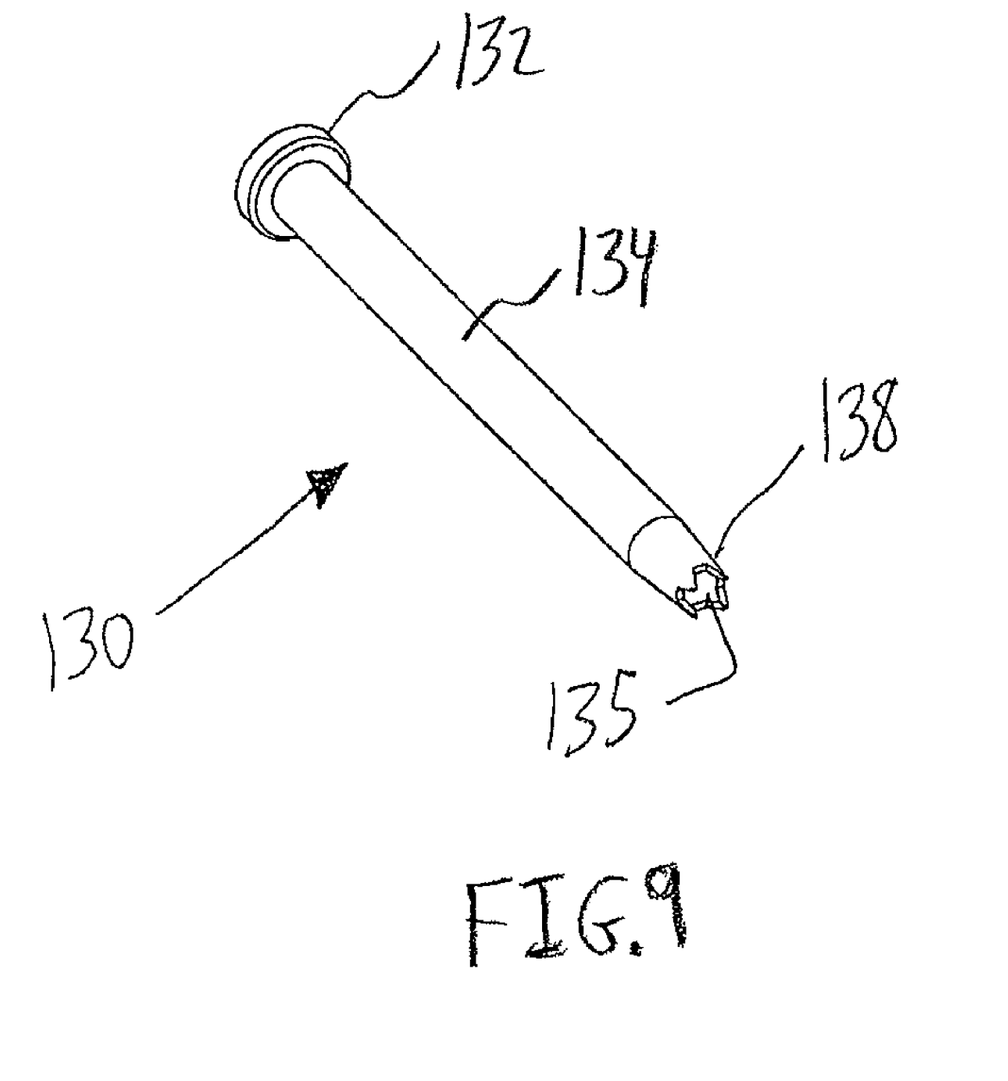
FIG. 9 is a perspective view of a pin guide bushing for use in the assembly of the invention.

In the embodiment of FIG. 9, the bushing 130 has a flared head portion 132, a bone end 138, and a cylindrical elongated body 134 extending between the head portion 132 and the end 138. The cylindrical elongated body 134 has a pin bore 135 therethrough. The pin bore 135 is configured to closely receive a guide pin 180 for use in driving the pin 180 into the femoral neck 202 along the pin path P. The bone end 138 of the bushing 130 is tapered and serrated.

Methods of setting a guide pin 180 using the instrument assembly of the invention will now be described. Using techniques known to those of skill in the art, the surgeon accesses a proximal end of the patient's femur. Because the instruments reference off of a medullary guide wire 190, an initial step in the method is to install the guide wire 190. Using techniques known to those of skill in the art, the surgeon places a guide wire 190, such as a 3.2 mm pin, in the piriformis fossa (along the greater trochanter) and drills the guide wire 190 toward the middle of the knee deep enough to obtain stable fixation. This establishes the position of the medullary guide wire 190, which will serve as a reference axis for the remainder of the procedure. As indicated in FIGS. 1-2, the goniometer 50 is configured such that only a short portion of the proximal end of the medullary guide wire 190 is needed for mounting the goniometer 50 on the guide wire 190. This feature reduces exposure of wire 190 above the femur, which facilities minimally invasive procedures.

Figure 3:
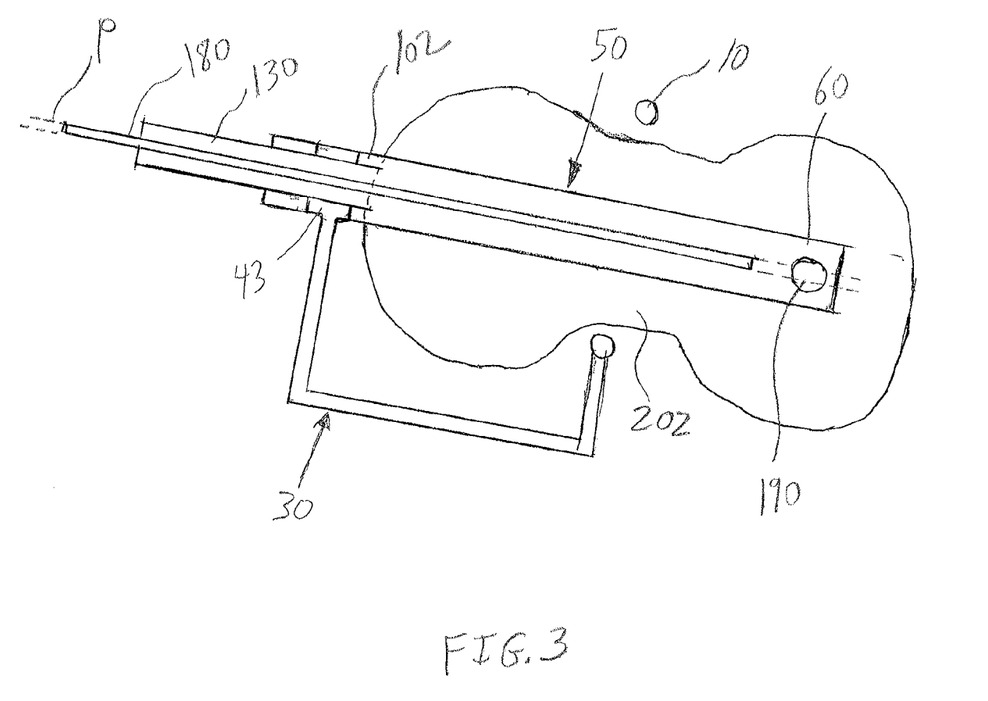
FIG. 3 is a representational view of one embodiment of an instrument assembly of the invention, shown in a transverse plane.

As indicated in the representational view of FIG. 2, the surgeon places a ring portion 12 of a femoral neck clamp 10 around the femoral neck 202. If necessary, osteophytes are removed from the femoral neck 202. As indicated in FIG. 2, the ring portion 12 should be as tight as possible. As can be seen by comparing FIG. 2 and FIG. 3, the ring portion 12 tightly encircles the femoral neck in the coronal plane (FIG. 2) but not in the transverse plane (FIG. 3). Nonetheless, the tight fit in the coronal plane establishes the neck center C in all planes.

The pin guide 30 is attached to the extension portion 20 of the femoral neck clamp 10. The foregoing step can be performed either before or after setting the femoral neck clamp 10 on the femoral neck 202. The configuration of the attachment base 32 and associated components discussed herein with reference to FIGS. 7-8 facilitates attachment of the pin guide 30 to the femoral neck clamp 10.

As shown in the representational views of FIGS. 2-3, the pin guide portion 44 of the pin guide 30 serves to establish a path P that passes through the neck center C defined by the femoral clamp 10. As indicated in FIGS. 1-2, the medullary guide wire engagement member 60 is inserted over the proximal protruding end of the medullary guide wire 190, such that the medullary guide wire bore 62 is axially aligned with the medullary guide wire 190. As indicated in FIG. 1, the pin guide engagement portion 102 of the goniometer 50 is positioned to engage the pin guide portion 43 of the pin guide 30. Due to the adjustment features provided by the four bar linkage arrangement of the embodiment shown in FIG. 1, the goniometer 50 can be readily adjusted to accommodate the size of the particular patient, while still maintaining a specific guide wire angle between the pin path P and the medullary guide wire 190. Further, the angle adjustment member 90 can be adjusted to select a particular guide wire angle, such as 140 degrees, relative to the medullary guide wire 190.

As indicated in FIGS. 1-2, the bushing 130 is threaded through the bushing bore 45 of the pin guide 30 and the upper and lower bushing bores 106A, 106B of the goniometer 50, which serves to link the goniometer 50 to the pin guide 30. With the assembly linked in place, the surgeon can finalize alignment of the pin path P by rotating the goniometer 50 about the medullary guide wire 190, and also by rotating the pin guide 30 about the femoral neck clamp 10. The pin path P is ultimately established by the orientation of the bushing bore 45 of the pin guide 30. Due to the configuration of the assembly, the pin path P always passes through the neck center C defined by the femoral neck clamp 10. The pin path P also always remains at the particular selected guide wire angle (e.g. 140 degrees) with respect to the medullary guide wire 190. The surgeon will typically aim to orient the pin path P in the center of the femoral neck, which serves to optimize neck strength, preserve natural anatomic orientation, and minimize the risk of notching during the subsequent step of preparing the femoral head to receive the resurfacing implant. However, the assembly of the invention allows adjustments to be made as needed. For example, if the patient's femoral neck 202 is excessively anteverted, the surgeon can reduce the anteversion by repositioning the guide path P accordingly. The medullary guide wire 190 angle, which establishes varus/valgus positioning, is typically selected by preoperative templating to pass through the center of the femoral neck. In the embodiment of FIGS. 5-6, the angle adjustment member 90 can be pre-adjusted to a selected guide wire angle, such as 135, 140 or 145 degrees, derived from pre-operative templating. However, if necessary, the selected guide wire angle can be reset to a different angle after the assembly is in place on the patient.

Once the desired pin path P is established, the surgeon drills the guide pin 180 through the pin guide bushing 130. The guide pin 180 should be drilled through the lateral cortex in order to insure stable internal fixation during the subsequent step of using the guide pin 180 to prepare the femoral head 204 for receipt of a femoral head implant. Note that because the position of the guide pin 180 is established with reference to the femoral neck 202, the femoral head 204 is ignored during alignment and installation of the guide pin 180.

Once the guide pin 180 is in the femoral neck 202, the instrument assembly is removed from the patient. Removal can be accomplished simply by removing the bushing 130, removing the goniometer 50, and unfastening the femoral neck clamp 10. Once the assembly has been removed from the patient, the surgeon uses the guide pin 180 to prepare the femoral head 204, using any of the various resurfacing procedures and instruments known to those of skill in the art.

The sequence of steps can be varied without departing from the spirit and scope of the invention. For example, the femoral neck clamp 10 can be fitted on the femoral neck 202 before insertion of the medullary guide wire 190 into the femur 200.

The assembly may be provided in the form of a kit comprising the various components discussed herein. The components of the kit are preferably arranged in a convenient format, such as in a surgical tray or case. However, the kit components do not have to be packaged or delivered together, provided that they are assembled or collected together in the operating room for use at the time of surgery.

Although the present invention has been described in terms of specific embodiments, it is anticipated that alterations and modifications thereof will no doubt become apparent to those skilled in the art. It is therefore intended that the following claims be interpreted as covering all alterations and modifications that fall within the true spirit and scope of the invention.

What is claimed is:

1. An instrument assembly for placing a guide pin in a femoral neck of a patient with reference to a medullary guide wire for use in resurfacing a femoral head, the assembly comprising:
    a femoral neck clamp configured to define a neck center of said femoral neck, the femoral neck clamp including a ring portion and an extension portion extending from the ring portion, the ring portion including a first partial ring portion and a second partial ring portion, the first partial ring portion having a first extension portion extending therefrom, the second partial ring portion having a second extension portion extending therefrom, the first and second extension portions pivotally attached to one another, the extension portion of the femoral neck clamp including a track for receiving an attachment base of the pin guide in a rotatable relationship,
    a pin guide attached to the femoral neck clamp, the pin guide having a pin guide portion, the pin guide portion configured to define a pin guide path passing through the neck center defined by the femoral neck clamp,
    a goniometer, the goniometer having a medullary guide wire engagement member and a pin guide engagement portion, the pin guide engagement portion adjustably linked to the medullary guide wire engagement member so as to accommodate patients of various sizes, the pin guide engagement portion configured to maintain a set angle with respect to said medullary guide wire, and
    the pin guide engagement portion and the pin guide portion configured to engage one another such that the goniometer orients the pin path at the set angle with respect to said medullary guide wire,
    wherein the pin guide is rotatably attached to the femoral neck clamp such that the pin guide portion can be selectively rotated through a plurality of pin path angles while maintaining the pin path through the neck center defined by the femoral neck clamp, wherein the track includes a tine groove for engaging the at least one tine of the attachment base of the pin guide to thereby selectively secure the pin guide in the track of the femoral neck clamp.

2. The instrument assembly of claim 1, wherein the goniometer further comprises an angle adjustment member, the angle adjustment member configured to adjust the pin guide engagement portion between a plurality of set angles.

3. The instrument assembly of claim 2, wherein the angle adjustment member is configured to adjust the pin guide engagement portion between three set angles, the angles being 135 degrees, 140 degrees and 145 degrees with respect to said medullary guide wire.

4. The instrument assembly of claim 1, wherein the pin guide engagement portion of the goniometer and the pin guide portion of the pin guide are configured to receive a pin guide bushing therethrough.

5. The instrument assembly of claim 1, wherein the track includes a pair of opposing stops for abutting against a stop member of the pin guide attachment base to thereby establish a rotation range for the pin guide relative to the femoral neck clamp.

6. The instrument assembly of claim 1, wherein the medullary guide wire engagement member has a medullary guide wire bore passing therethrough, the medullary guide wire bore configured to closely receive said medullary guide wire.

7. The instrument assembly of claim 6, wherein the pin guide engagement portion is adjustably linked to the medullary guide wire engagement member via a four bar linkage.

8. The instrument assembly of claim 7, wherein the four bar linkage includes the medullary wire engagement member, a support member, and a central member between the medullary wire engagement member and the support member, the central member pivotally linked to the medullary wire engagement member via a first upper linkage bar and a first lower linkage bar, the central member pivotally linked to the support member via a second upper linkage bar and a second lower linkage bar.

9. The instrument assembly of claim 8, wherein the support member has an adjustment portion and an angle adjustment member, the angle adjustment member configured for selecting between a plurality of set angles.

10. The instrument assembly of claim 9, wherein the angle adjustment member is pivotally engaged to the adjustment portion.

11. An instrument assembly for placing a guide pin in a femoral neck of a patient with reference to a medullary guide wire for use in resurfacing a femoral head, the assembly comprising:

a femoral neck clamp configured to define a neck center of said femoral neck, the femoral neck clamp including a ring portion and an extension portion extending from the ring portion, the ring portion including a first partial ring portion and a second partial ring portion, the first partial ring portion having a first extension portion extending therefrom, the second partial ring portion having a second extension portion extending therefrom, the first and second extension portions pivotally attached to one another, the extension portion of the femoral neck clamp including a track for receiving an attachment base of the pin guide in a rotatable relationship, a pin guide attached to the femoral neck clamp, the pin guide having a pin guide portion, the pin guide portion configured to define a pin guide path passing through the neck center defined by the femoral neck clamp, a goniometer, the goniometer having a medullary guide wire engagement member and a pin guide engagement portion, the pin guide engagement portion adjustably linked to the medullary guide wire engagement member so as to accommodate patients of various sizes, the pin guide engagement portion configured to maintain a set angle with respect to said medullary guide wire, and the pin guide engagement portion and the pin guide portion configured to engage one another such that the goniometer orients the pin path at the set angle with respect to said medullary guide wire, wherein the pin guide is rotatably attached to the femoral neck clamp such that the pin guide portion can be selectively rotated through a plurality of pin path angles while maintaining the pin path through the neck center defined by the femoral neck clamp, wherein the pin guide has an attachment base, the attachment base having a bore therethrough, at least one tine in the attachment base, a stop member extending from the attachment base, an extension portion, the extension portion having a first leg extending from the attachment base and a second leg extending at an angle from the first leg, and the pin guide portion positioned at an end of the second leg, the pin guide portion having a bushing holder having a bushing bore therethrough, and a lengthwise slot.

12. An instrument assembly for placing a guide pin in a femoral neck of a patient with reference to a medullary wide wire for use in resurfacing a femoral head, the assembly comprising:

a femoral neck clamp configured to define a neck center of said femoral neck, a pin guide attached to the femoral neck clamp, the pin guide having a pin guide portion, the pin guide portion configured to define a pin guide path passing through the neck center defined by the femoral neck clamp, a goniometer, the goniometer having a medullary guide wire engagement member and a pin guide engagement portion, the pin guide engagement portion adjustably linked to the medullary guide wire engagement member so as to accommodate patients of various sizes, the pin guide engagement portion configured to maintain a set angle with respect to said medullary guide wire, the medullary guide wire engagement member having a medullary guide wire bore passing therethrough, the medullary guide wire bore configured to closely receive the medullary guide wire, and the pin guide engagement portion and the pin guide portion configured to engage one another such that the goniometer orients the pin path at the set angle with respect to said medullary guide wire, wherein the pin guide is rotatably attached to the femoral neck clamp such that the pin quide portion can be selectively rotated through a plurality of pin path angles while maintaining the pin path through the neck center defined by the femoral neck clamp, wherein the pin guide engagement portion is adjustably linked to the medullary guide wire engagement member via a four bar linkage, the four bar linkage including the medullary wire engagement member, a support member, and a central member between the medullary wire engagement member and the support member, the central member pivotally linked to the medullary wire engagement member via a first upper linkage bar and a first lower linkage bar, the central member pivotally linked to the support member via a second upper linkage bar and a second lower linkage bar, wherein the support member has an adjustment portion and an angle adjustment member, the angle adjustment member configured for selecting between a plurality of set angles, wherein the adjustment portion has a first angle indent, a second angle indent and a third angle indent, and the angle adjustment member has at least one detent, the at least one detent positioned to selectively engage at least two of the first, second and third angle indents for use in selecting a set angle from among the plurality of set angles.

13. The instrument assembly of claim 12, wherein the angle adjustment member has an upper detent and a lower detent.

14. The instrument assembly of claim 13, wherein the angle adjustment member has an upper detent housing and a lower detent housing, the upper and the lower detent housings fixedly positioned on opposing sides of the angle adjustment member.

15. The instrument assembly of claim 13, wherein the upper and lower detents are spring biased plunger detents.

16. The instrument assembly of claim 12, wherein the pin guide engagement portion has an upper arm and a lower arm, the upper and lower arms, defining an opening for receipt of a bushing holder of the pin guide,
  the upper arm having an upper bushing holder adjacent an end thereof, the upper bushing holder having an upper bushing bore formed therethrough,
  the lower arm having a lower bushing holder adjacent an end thereof, the lower bushing holder having a lower bushing bore formed therethrough, and
  the upper and lower bushing bores axially aligned for receipt of a bushing.

17. The instrument assembly of claim 16, further comprising a pin guide bushing, the pin guide bushing having a flared head portion, a bone end, and a cylindrical elongated body extending between the head portion and the bone end, the cylindrical elongated body having a through bore therethrough, the through bore configured to closely receive said guide pin.

18. The instrument assembly of claim 17, wherein the bone end of the pin guide bushing is tapered and serrated.

* * * * *